US010126218B2

(12) United States Patent
Toner et al.

(10) Patent No.: US 10,126,218 B2
(45) Date of Patent: Nov. 13, 2018

(54) CAPTURING PARTICLES

(71) Applicant: The General Hospital Corporation, Boston, MA (US)

(72) Inventors: Mehmet Toner, Charlestown, MA (US); Shannon Stott, Stoneham, MA (US); Chia-Hsien Hsu, Zhunan Town (TW)

(73) Assignee: The General Hospital Corporation, Boston, MA (US)

( * ) Notice: Subject to any disclaimer, the term of this patent is extended or adjusted under 35 U.S.C. 154(b) by 158 days.

(21) Appl. No.: 14/843,028

(22) Filed: Sep. 2, 2015

(65) Prior Publication Data
US 2015/0377753 A1    Dec. 31, 2015

Related U.S. Application Data

(63) Continuation of application No. 13/121,130, filed as application No. PCT/US2009/058408 on Sep. 25, 2009, now Pat. No. 9,128,091.

(Continued)

(51) Int. Cl.
*G01N 1/40* (2006.01)
*B01L 3/00* (2006.01)
(Continued)

(52) U.S. Cl.
CPC ........ *G01N 1/405* (2013.01); *B01L 3/502761* (2013.01); *G01N 33/54366* (2013.01); *G01N 33/56966* (2013.01); *G01N 33/57434* (2013.01); *B01L 2200/0647* (2013.01); *B01L 2200/0668* (2013.01); *B01L 2300/0816* (2013.01);
(Continued)

(58) Field of Classification Search
CPC ............. G01N 1/405; G01N 33/56966; G01N 33/57434; G01N 33/54366
See application file for complete search history.

(56) References Cited

U.S. PATENT DOCUMENTS

| | | |
|---|---|---|
| 3,788,557 A | 1/1974 | Breunsbach |
| 6,692,952 B1 | 2/2004 | Braff et al. |

(Continued)

FOREIGN PATENT DOCUMENTS

| | | |
|---|---|---|
| EP | 1860443 | 11/2007 |
| WO | WO06/102675 | 9/2006 |

OTHER PUBLICATIONS

C-H. Hsu et al. "Microvortex for focusing, guiding and sorting of particles." Lab on a Chip vol. 8:2128-2134 (Published on line Oct. 30, 2008).

(Continued)

*Primary Examiner* — Melanie Yu Brown
(74) *Attorney, Agent, or Firm* — Fish & Richardson P.C.

(57) ABSTRACT

Methods and systems capturing particles suspended in a fluid flowed through a micro-channel, can include flowing the fluid including the particles to be captured through a micro-channel and past a groove defined in a surface of a wall of the micro-channel such that flowing the fluid past the groove forms microvortices in the fluid; contacting at least some of the particles against an adherent disposed on one or more of walls of the microchannel after the microvortices form in the fluid; and capturing at least some of the particles contacting the adherent.

14 Claims, 16 Drawing Sheets

Related U.S. Application Data

(60) Provisional application No. 61/100,420, filed on Sep. 26, 2008.

(51) Int. Cl.
   *G01N 33/543* (2006.01)
   *G01N 33/569* (2006.01)
   *G01N 33/574* (2006.01)

(52) U.S. Cl.
   CPC .................. *B01L 2300/0858* (2013.01); *B01L 2400/0487* (2013.01); *B01L 2400/086* (2013.01)

(56) References Cited

U.S. PATENT DOCUMENTS

| | | |
|---|---|---|
| 6,907,895 B2 | 6/2005 | Johnson et al. |
| 7,658,536 B2 | 2/2010 | Johnson et al. |
| 8,122,909 B2 | 2/2012 | Tonkovich et al. |
| 2002/0076727 A1 | 6/2002 | Cardone et al. |
| 2003/0087292 A1 | 5/2003 | Chen et al. |
| 2003/0104170 A1 | 6/2003 | Johnston et al. |
| 2003/0178641 A1 | 9/2003 | Blair et al. |
| 2003/0186027 A1 | 10/2003 | Tajima et al. |
| 2004/0018611 A1 | 1/2004 | Ward et al. |
| 2004/0258571 A1 | 12/2004 | Lee et al. |
| 2007/0017633 A1 | 1/2007 | Tonkovich et al. |
| 2009/0036324 A1 | 2/2009 | Fan et al. |
| 2010/0304485 A1* | 12/2010 | Karnik .................. C12N 5/0068 435/375 |
| 2011/0294187 A1 | 12/2011 | Toner et al. |

OTHER PUBLICATIONS

Jennifer O. Foley et al "Experimental and model investigation of the time-dependent 2-dimensional distribution of binding in a herringbone microchannel", Lab on a Chip, vol. 8, No. 4, pp. 557-564 (Apr. 1, 2008).

Hsu-Yi Lee et al: "Optimizing Micromixer Design for Enhancing Dielectrophoretic Microconcentrator Performance", Analytical Chemistry, vol. 79, No. 5, pp. 1833-1839 (Mar. 1, 2007).

Peter B. Howell et al.: "A microfluidic mixer with grooves placed on the top and bottom of the channel", Lab on a Chip, vol. 5, No. 5, pp. 524-530 (May 1, 2005).

Examination report dated Mar. 9, 2012 for corresponding application EP 09816915.4.

EP Search report dated Feb. 22, 2012 for corresponding application EP 09816915.4.

Search Report and Written Opinion dated Apr. 27, 2010 from corresponding application PCT/US2009/058408.

Abraham D. Stroock et al., Chaotic Mixer for Microchannels, Science, vol. 295, Jan. 25, 2002, pp. 647-651.

Ng et al. "Components for Integrated Poly(dimethylsiloxane) Microfluidic Systems" Electrophoresis 2002, 23, 3461-3473.

Williams et al. "A Practical Guide to the Staggered Herringbone Mixer" NIH-PA Author Manuscript: PMC Dec. 13, 2009, 1-19; published in final edited form as Lab Chip Jul. 2008 ; 8(7) 1121-1129.

\* cited by examiner

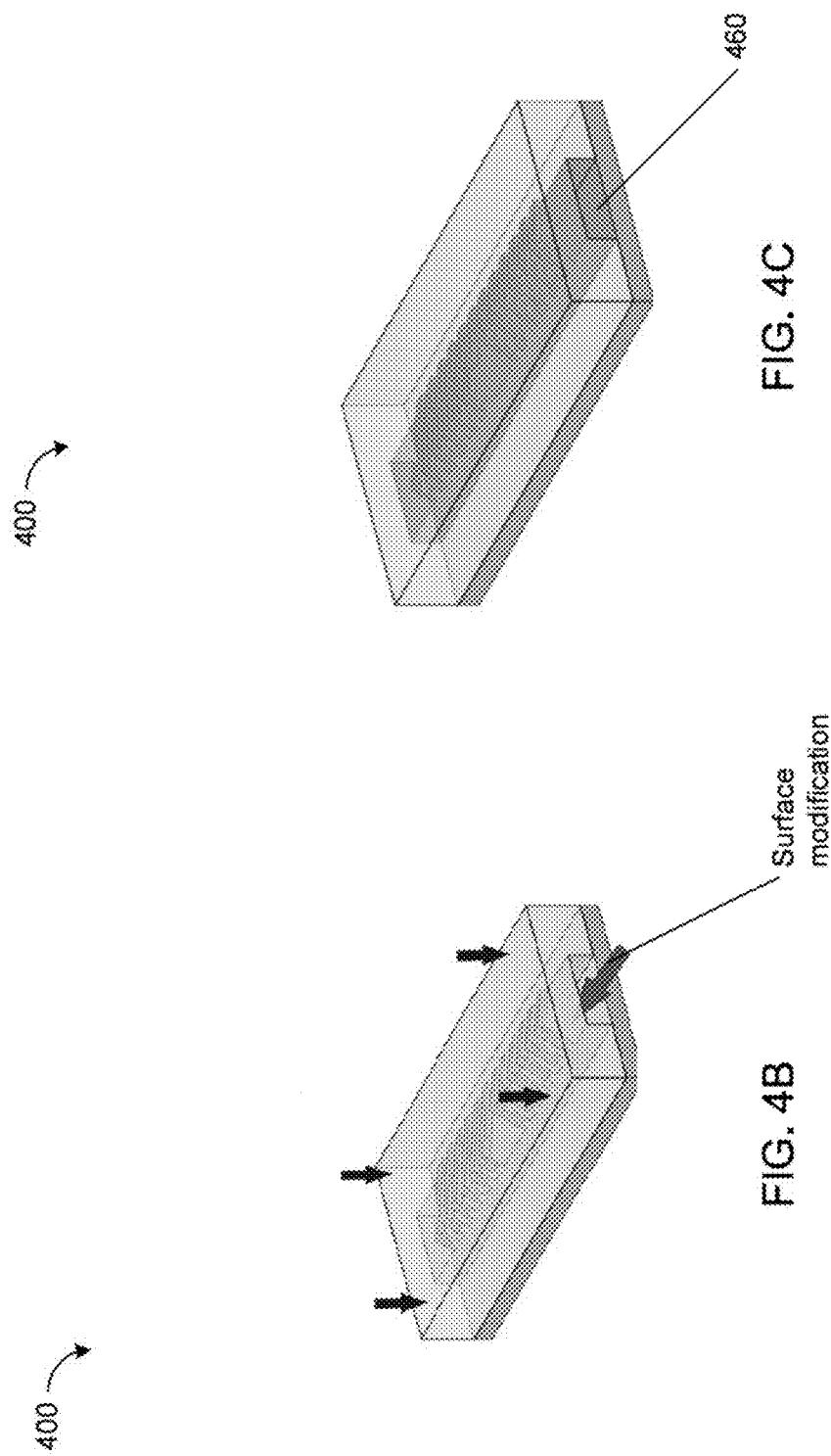

CAPTURING PARTICLES

CROSS-REFERENCE TO RELATED APPLICATIONS

This application is a continuation of U.S. application Ser. No. 13/121,130, filed Aug. 11, 2011, which is a 371 U.S. National of PCT Application No. PCT/US2009/058408, filed Sep. 25, 2009, which claims priority to U.S. Patent Application No. 61/100,420, entitled Microvortex for focusing, guiding and sorting of particles which was filed on Sep. 26, 2008, the entire contents of which are incorporated herein by reference in their entirety.

BACKGROUND

Microfluidic devices find application in micro total analysis systems (μTAS) or lab-on-a-chip (LOC) systems because such devices offer the ability to analyze small sample volumes, and can be developed into highly parallel systems at reduced costs. In particular, such systems can be used in biological and clinical applications in which particle manipulation is used to perform operations, for example, concentrating, detecting, sorting, and focusing particulate samples, such as cells and colloids. Passive manipulation of particles flowing through microfluidic devices, by techniques such as hydrodynamic focusing, size filtration, and sedimentation, is relatively simple in comparison to active manipulation using external energy such as optical forces, magnetism, electro-kinetics, dielectrophoresis, acoustics, and the like. Passive manipulation does not rely on external sources of energy, but instead can be accomplished using geometries of micro-channels in devices, and flow conditions through such channels. In contrast, active manipulation can employ external sources of energy and can require the integration of powered components to the microfluidic devices.

SUMMARY

This specification describes technologies relating to affinity-based particle capture in microfluidic devices having grooves. When we refer to grooves, we include, for example, long narrow channels (e.g., channels formed extending into and defined by a wall of a larger channel).

In one aspect, methods for capturing particles suspended in a fluid flowed through a micro-channel include: flowing the fluid including the particles to be captured through a micro-channel and past a groove defined in a surface of a wall of the micro-channel; contacting at least some of the particles against an adherent disposed on one or more of walls of the microchannel; and capturing at least some of the particles contacting the adherent.

In one aspect, microfluidic devices include: a micro-channel including: an inlet, an outlet positioned at a distance from the inlet, wherein fluid flows from the inlet to the outlet, and a groove defined into a surface of a wall of the microchannel, the groove including an apex and two ends, each end connected to the apex, the groove oriented such that the fluid flows past the ends towards the apex; and an adherent applied to at least one wall to selectively attach an analyte of interest.

Embodiments can include one or more of the following features alone or in various combinations.

In some embodiments, the adherent is disposed on the surface of the wall in which the groove is defined.

In some embodiments, the groove is defined in a wall of the micro-channel. In some cases, the groove extends into the wall.

In some embodiments, the groove and a plurality of additional grooves are defined in a surface of the wall such that flowing the fluid past the plurality of additional grooves forms respective microvortices in the fluid.

In some embodiments, flowing the fluid past the groove comprises flowing the fluid past a groove including an apex and two ends, each end connected to the apex, the groove oriented such that the fluid flows past the ends towards the apex. In some cases, the apex and the two ends are defined in the surface in a V shape. A dimension of the groove can be in a range between 3 μm and 70 μm.

In some embodiments, flowing the fluid comprises flowing the fluid at an average flow velocity between 2.4 cm/min and 6.0 cm/min.

In some embodiments, the particles are cancer cells and the adherent is an antibody configured to bind the cancer cells. In some cases, methods also include culturing the captured cancer cells.

In some embodiments, flowing the fluid past the groove forms microvortices in the fluid.

In some embodiments, the adherent is an antibody.

In some embodiments, the adherent is an aptamer.

In some embodiments, the inlet is configured to receive the fluid that includes the analyte.

In some embodiments, the apex and the two ends form a V-shape.

In some embodiments, the groove spans less than a width of the micro-channel.

In some embodiments, each of the two ends are equidistant from the apex.

In some embodiments, the groove is formed symmetrically in the surface of the wall such that the apex is positioned on an axis passing through a center of the micro-channel and the two ends are equidistantly positioned from the apex.

In some embodiments, a first of the two ends is positioned nearer to the apex than a second of the two ends.

In some embodiments, the apex is offset from an axis extending along a center of the micro-channel.

In some embodiments, the groove is positioned such that a first end of the groove receives the fluid before a second end.

In some embodiments, the groove is one of a plurality of grooves defined in the wall of the micro-channel, each of the plurality of grooves having an apex and two ends.

In some embodiments, the plurality of grooves are disposed in a column of grooves.

In some embodiments, the device further comprises include an additional column of grooves formed adjacent the column of grooves.

In some embodiments, an apex and two ends of a groove in the column of grooves are aligned with an apex and two ends of a groove in the additional column of grooves on corresponding planes that are perpendicular to an axis passing through the micro-channel.

In some embodiments, the additional column of grooves is offset from the column of grooves.

In some embodiments, a dimension of a groove projecting outward of the micro-channel is in a range between 3 μm and 70 μm.

Particular implementations of the subject matter described in this specification can be implemented to realize one or more of the following advantages. The techniques described here can increase a potential for the passive manipulation and capture of particles suspended in a fluid, for example, cells suspended in a buffer solution, in a microfluidic environment. The grooves formed in the microchannel of the microfluidic device can induce helical flows that generate microvortices in the fluid flowing through the channel. The microvortices can be exploited to enhance the transverse movement of particles flowing axially through the channel, towards channel walls, causing the particles to more frequently interact with and bind to the walls. In comparison to microfluidic devices having micro-channels without the grooves, cell-substrate interactions can be increased when cells suspended in a buffer solution are flowed through the micro-channel that includes the grooves. This, in turn, can increase the capture efficiency of the device. Further, passive microfluidic fluid manipulation techniques described here can negate the need for external sources of energy, and can consequently decrease energy consumption and cost of manufacture, particularly when the microfluidic device is scaled up to highly parallel μTAS or LOC systems or both. The devices can be transparent based on the choice of materials for manufacturing. The volumes of samples and reagents consumed can be decreased due to the micrometer-range dimensions through which the volumes are flowed. Consequently, cost of samples and reagents can also be decreased. The techniques described are applicable to capture and culture live cells.

The details of one or more implementations of the specification are set forth in the accompanying drawings and the description below. Other features, aspects, and advantages of the specification will become apparent from the description, the drawings, and the claims.

BRIEF DESCRIPTION OF THE DRAWINGS

FIGS. 4A-4C illustrate an exemplary method of forming the microfluidic device of FIG. 1.

Like reference numbers and designations in the various drawings indicate like elements.

DETAILED DESCRIPTION

Methods, apparatuses, and systems for affinity-based particle capture in microfluidic devices having grooves are described. A micro-channel formed in a microfluidic device can be treated to capture particles suspended in a fluid flowing through the channel. A particle capture efficiency of the microfluidic device can be defined as a ratio of a number of particles captured in the channel and a total number of particles flowed through the channel. As described below, grooves are formed extending into the walls of the micro-channel to create flow patterns in the fluid that promote an interaction between the particles suspended in the fluid and inner surfaces of the walls of the channel. The increased interaction can lead to an increase in a number of particles captured in the channel, and consequently, in the particle capture efficiency of the microfluidic device. The efficiency can further be increased by tailoring structural features of the microfluidic device including, for example, device substrate material, channel and groove dimensions, and the like, as well as fluid flow parameters such as flow rates based on types of particles and the types of fluids in which the particles are suspended. An example of such a microfluidic device manufactured using soft lithography techniques is described with respect to FIG. 1. As described later, particles are captured in the micro-channel of the microfluidic device by forming grooves in a wall of the micro-channel, coating an adherent on the inner surfaces of the walls of the micro-channel, and flowing particles suspended in the fluid through the micro-channel.

Figure 1:
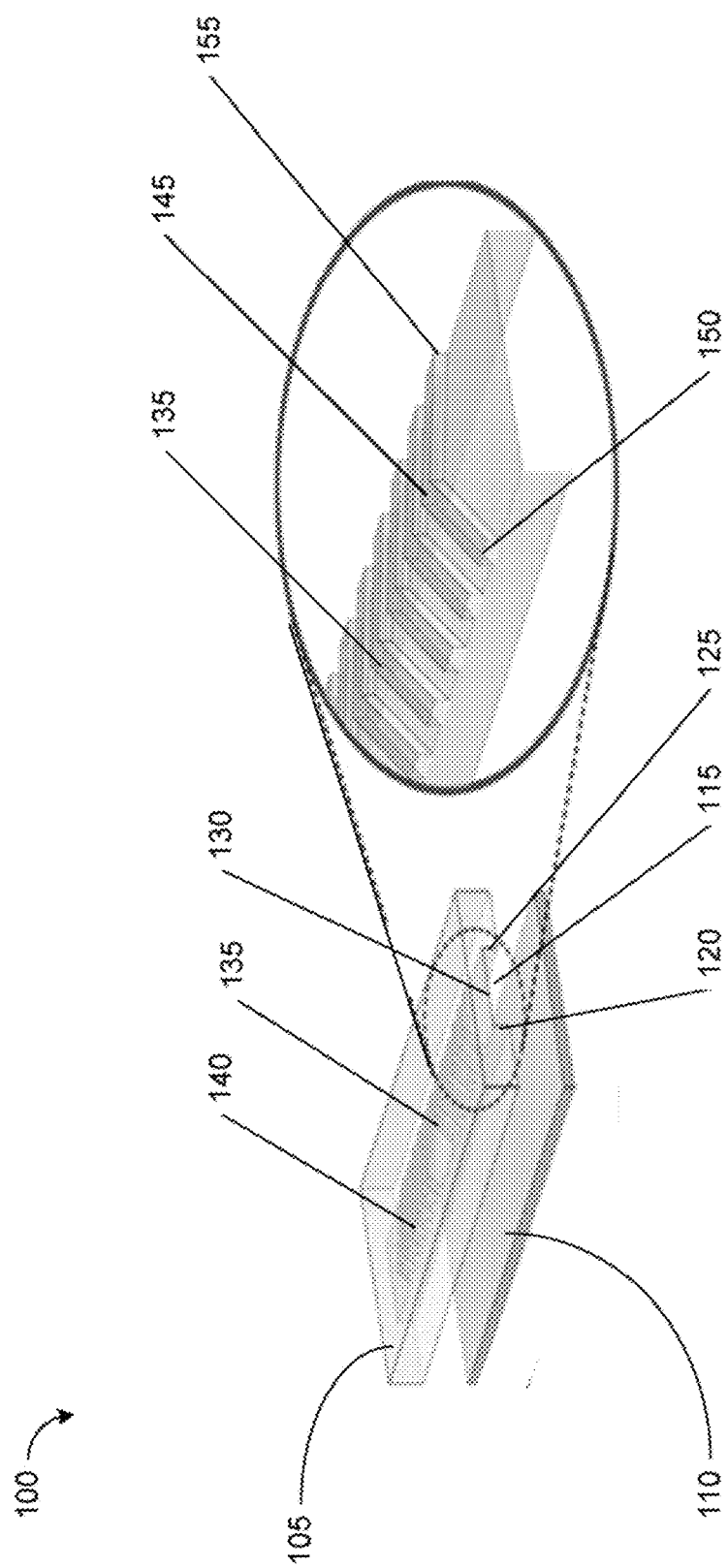
FIG. 1 shows an embodiment of a microfluidic device having grooves.

FIG. 1 illustrates a microfluidic device 100 having grooves 135, 140 extending into one of the walls defining a channel 115 of the device 100. In some embodiments, microfluidic devices include protrusions extending outward from the wall (e.g., V-shaped protrusions) rather than grooves extending into a wall of the channel 115. In some implementations, a microfluidic device 100 can include an upper substrate 105 bonded to a lower substrate 110, each of which can be fabricated using an appropriate material. For example, the upper substrate 105 can be fabricated using an elastomer such as, for example, polydimethylsiloxane (PDMS), and the lower substrate can be fabricated using glass, PDMS, or another elastomer. Alternatively, or in addition, the substrates can be manufactured using plastics such as, for example, polymethylmethacrylate (PMMA), polycarbonate, cyclic olefin copolymer (COC), and the like. In general, the materials selected to fabricate the upper and lower substrates can be easy to manufacture, for example, easy to etch, and can offer optical properties that facilitate ease of testing, for example, can be optically clear, and can be non-toxic so as to not negatively affect the cells attached to the substrate. In addition, the materials are preferred to exhibit no or limited autofluorescence. Further, the materials can be easy to functionalize so that analytes can be attached to the substrate. Furthermore, the materials can be mechanically strong to provide strength to the microfluidic device 100. The upper substrate 105 can be securely fastened to the lower substrate 110, with a micro-channel formed between them, as described below.

In some implementations, the micro-channel 115 can have a rectangular cross-section including two side walls 120 and 125, and an upper wall 130 formed in the upper substrate 105. Terms of relative location such as, for example, "upper" and "lower" are used for ease of description and denote location in the figures rather than necessary relative positions of the features. For example, the device can be oriented such that the grooves are on a bottom surface of the channel or such that a central axis of the channel extends vertically. Alternatively, the cross-section of the micro-channel 115 can be one of several shapes including but not limited to triangle, trapezoid, half-moon, and the like. The lower substrate 110 can form the lower wall of the micro-channel 115 once bonded to the upper substrate 105. In some implementations, the micro-channel 115 includes multiple grooves 135 formed in the upper wall 130 of the micro-channel 115. Alternatively, the grooves 135 can be formed in any of the walls, and/or can be formed in more than one wall of the micro-channel 115. The grooves 135 can span an entire length of a wall, or only a portion of the wall.

Figure 2A:
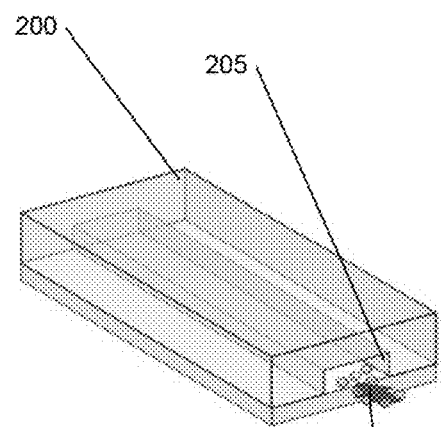
FIGS. 2A-2D illustrate particle flow paths in a micro-channel having flat walls and another micro-channel having grooves formed in a wall.
Figure 2B:
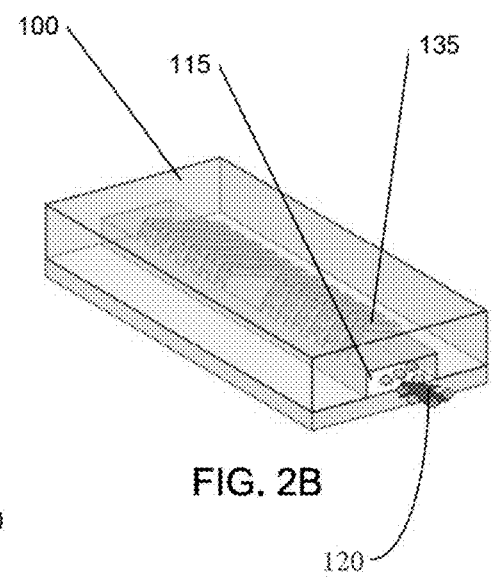

FIGS. 2A-2D are schematics illustrating particle suspensions flowing through a micro-channel having flat walls and another micro-channel having grooves formed in a wall. FIG. 2A shows a microfluidic device 200 that includes a micro-channel 205 having a rectangular cross-section. The walls of the micro-channel 205 do not include grooves such as those described with respect to the microfluidic device 100, i.e., surfaces of the walls are flat. A particle suspension 220 including particles 225 suspended in a fluid is flowing through the micro-channel 205. In contrast, FIG. 2B shows a similar suspension 120 flowing through the microfluidic device 100.

As the fluid flows past a herringbone pattern formed by arranging grooves 135 in a column in the micro-channel 115, the grooves 135 in the path of the fluid disrupt fluid flow. In some embodiments, depending upon flow velocity and the dimensions of the grooves, specifically, for example, a size of the grooves and an angle between the two arms of a groove, the disruption in the fluid flow leads to a generation of microvortices in the fluid. The microvortices are generated because the grooves induce fluid flow in a direction that is transverse to a principal direction of fluid flow, i.e., the axial direction. In some embodiments, although microvortices are not generated, the grooves 135, 140 induce sufficient disruption to alter the flow path of portions of the fluid to increase wall-particle interactions.

Figure 2C:
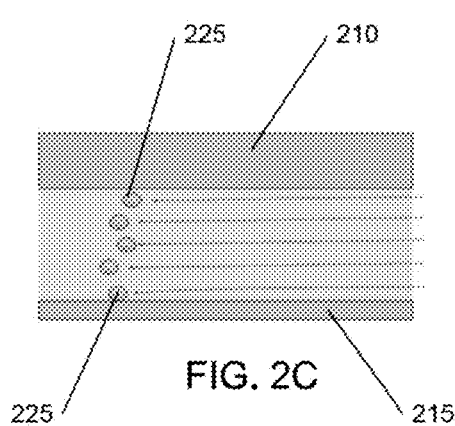
Figure 2D:
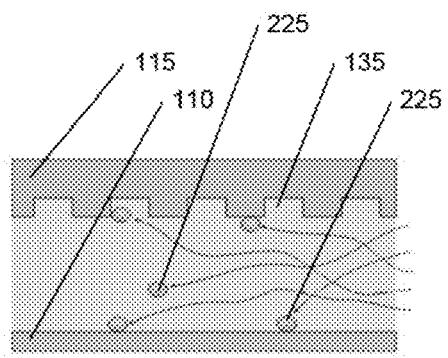

In an absence of the grooves, as shown in FIG. 2C, the particles 225 suspended in the fluid travel through the flat micro-channel 205 in a substantially linear fashion such that only those particles 225 near the edges of the flow field (e.g., immediately adjacent to the walls of the micro-channel 205) are likely to interact with the micro-channel 205 walls. In contrast, as shown in FIG. 2D, flowpaths of the particles 225 traveling past the herringbone patterns experience can be disrupted by the microvortices in the fluid, increasing the number of particle-micro-channel wall interactions. The microvortices are affected by the structural features of each groove 445 formed in the upper wall 130 of the microfluidic device 100. Exemplary dimensions of a groove 445 are described with reference to FIG. 3.

Figure 3A:
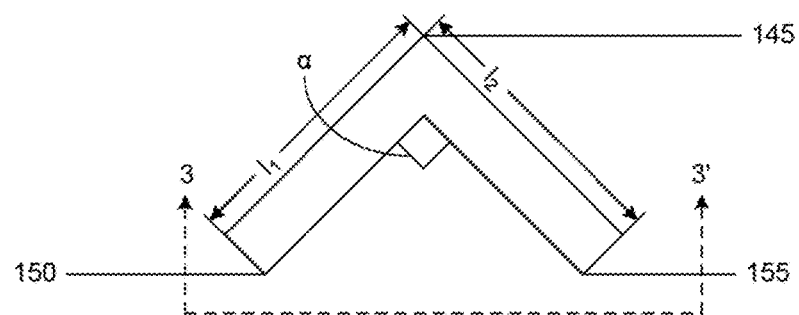
FIGS. 3A-3C illustrate exemplary grooves.
Figure 3B:
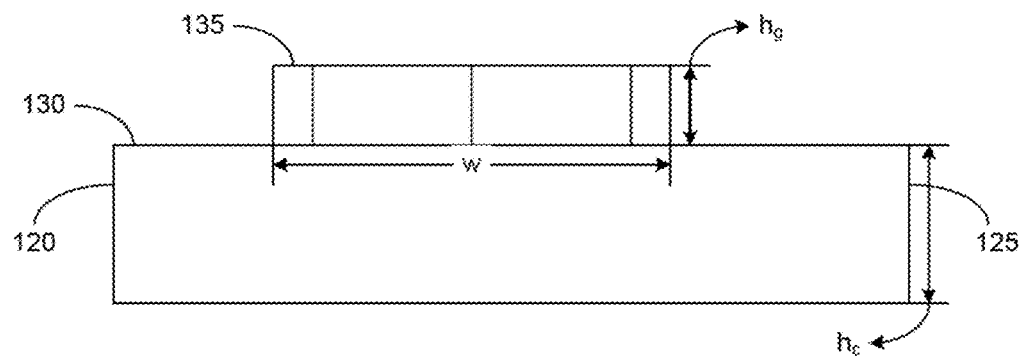

FIGS. 3A and 3B illustrate a groove 135 formed on an upper wall 130 of a micro-channel 115. As shown in FIG. 3A, a symmetric groove 135 includes two arms, each spanning a length between a first end 150 and the apex 145 ($l_1$), and a second end 155 and the apex 145 ($l_2$). In the illustrated embodiments, the angle α between the two arms is 90°. In some embodiments, the angle α between the arms ranges between 10° and 170°. FIG. 3B is a view of the micro-channel 115 including the groove 135 formed in the upper surface 115. As shown in FIG. 3B, the width of the groove is w, the height of the side walls 120 and 125 of the micro-channel 115 is $h_c$ and the height of the groove 135 formed on the upper wall 115 is $h_g$. In some embodiments, $l_1$ and $l_2$, each range between 250 μm-400 μm, $h_g$ ranges between 3 μm and 70 μm, $h_c$ is 100 μm. For example, when $h_g$ is 100 μm, $h_g$ is 25 μm.

Figure 3C:
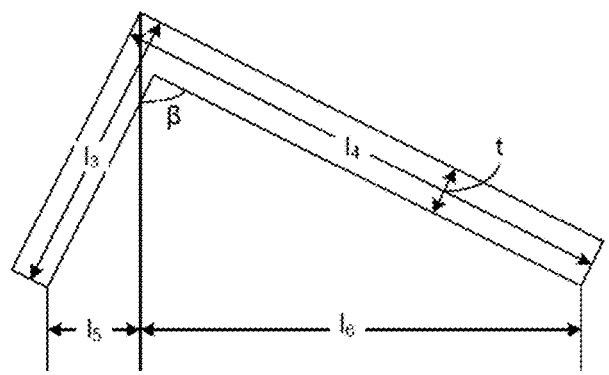

FIG. 3C illustrates an asymmetric groove 140 including two arms, each spanning a length between a first end 170 and an apex 165 ($l_3$), and a second end 175 and the apex ($l_4$), respectively. In the illustrated embodiment, the angle β between the two arms is 90°, and can range between 10° and 170°. In some implementations, the groove 140 can be manufactured such that a ratio between $l_3$ and $l_4$ is 0.5. For example, $l_3$ is 141 μm and $l_4$ is 282 μm. The groove 140 has a thickness of 35 μm. An effect of the height of the groove, $h_g$, on particle capture is described with reference to FIG. 15.

A herringbone pattern can be created by forming a column of herringbones in which each groove is positioned adjacent to another groove. Further, all grooves in the column can face the same direction. In some embodiments, a distance between each groove is 50 μm. Alternatively, the grooves can be positioned at any distance from each other. A column can include any number of grooves, for example, ten grooves. The herringbone pattern can further include multiple columns of grooves formed serially from an inlet to the outlet. In some embodiments, two adjacent columns of grooves can be separated by 100 μm. In other words, a first groove of the second column can be positioned 100 μm away from a last groove of the first column. This pattern can be repeated from an inlet to the micro-channel 115 to the outlet.

In some embodiments, grooves or groups of grooves in a column can be laterally offset from each other. For example, as can be see in FIG. 2B, the column of grooves in microfluidic device 100 includes a first set of grooves with apexes set to the right (facing downstream) of the channel centerline and a second set of grooves with apexes set to the left of the channel centerline. Such offsets are thought to further increase wall-particle interactions.

The dimensions shown in FIGS. 3A-3C are exemplary. In general, the choice of groove heights can depend on factors including channel dimensions, particle properties including size, density, and the like, and particle suspension flow rates. Although deeper grooves offer more disruption, other factors can impose limits on groove heights. For example, up to a certain limit, the groove height can be increased in proportion with the channel height. The channel height, and consequently the groove height, can depend upon the particle to micro-channel 115 surface contact area. An increase in channel dimensions can cause a decrease in particle-micro-channel 115 interactions as surface contact area available for the particles to interact decreases relative to the cross-sectional flow area. Also, a lower limit on the channel height, and consequently the groove height, can be imposed to prevent clogging. In some implementations, a ratio between groove height and channel height can be less than one, for example, in a range between 0.1 to 0.6. In some implementations, the ratio can be equal to one (e.g., the groove height can be equal to the channel height), or can be greater than one (e.g., the groove height, for example, 60 μm, can be greater than the channel height, for example, 50 μm). Further, the shape of the groove can be different from a "V" shape, for example, "U" shape, "L" shape, and the like.

The micro-channel 115 can be formed in the upper substrate 105, for example, using soft lithography techniques. In some implementations, negative photoresist (SU-8, MicroChem, Newton, Mass., USA) can be photolithographically patterned on silicon wafers to create masters with two-layer features. The masters thus formed can include SU-8 features that form the basis for the features of the micro-channel 115, for example, channel cross-section, channel size, and the like. The heights of SU-8 features (ranging from 3 µm-100 µm) on the masters can be measured with a surface profilometer such as a Dektak ST System Profilometer, commercially available from Veeco Instruments Inc., Plainview N.Y. The masters can then be used as molds on which PDMS pre-polymer can be poured and allowed to cure in a conventional oven at 65° C. for 24 hours. The upper substrate 105, including the micro-channel 115, is formed when the poured PDMS pre-polymer is cured. The cured upper substrate 110 can be removed from the molds and bonded to the lower substrate 105, for example using oxygen plasma treatment, to form the microfluidic device 100. Alternatively, other types of bonding, for example, using a reversible sealant, using physical clamping and holding under pressure, and the like, can be used. In some implementations, the substrates can be securely bonded together through chemical bonds, and can subsequently be separated by breaking the bonds under the application of mechanical forces.

Figure 4A:
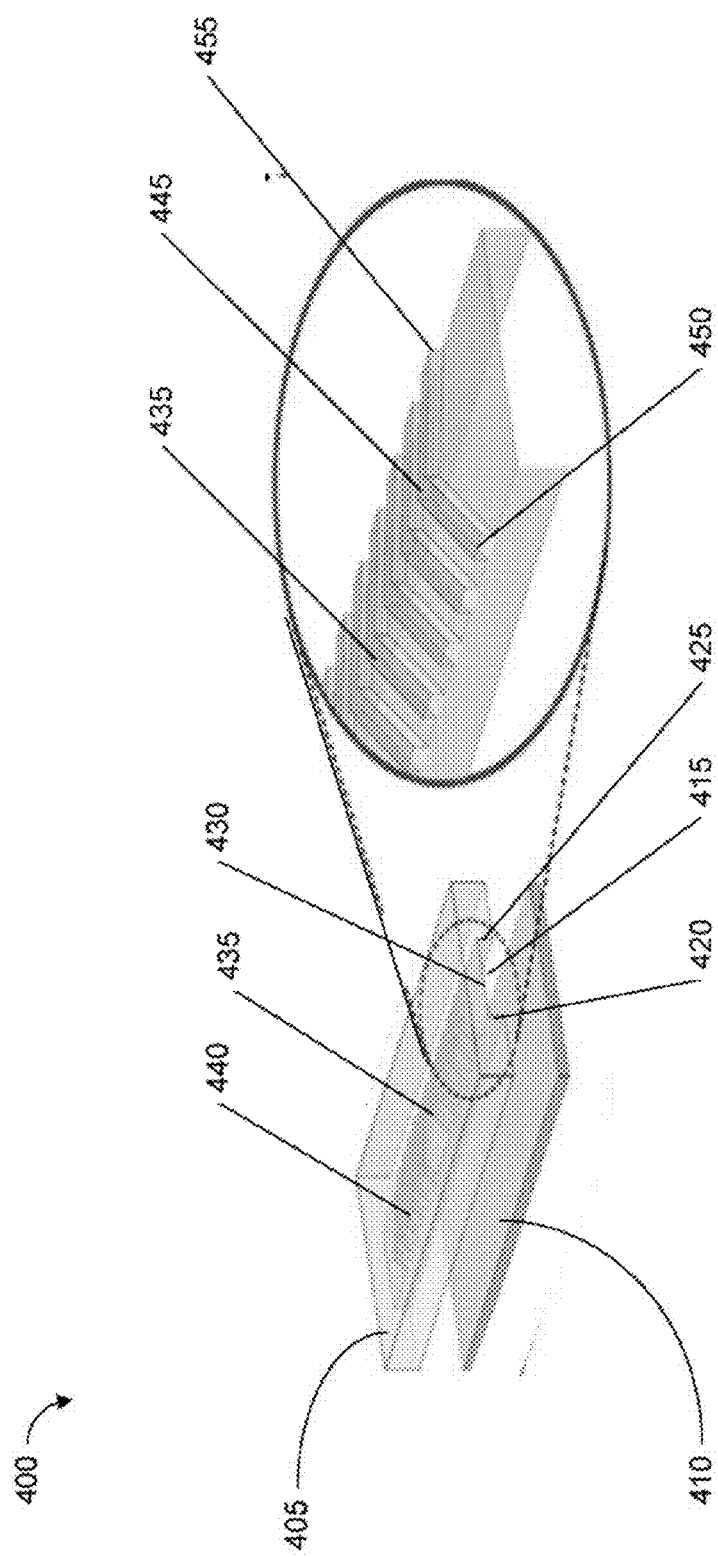

FIGS. 4A-4C illustrate the formation of a microfluidic device 100 including an upper substrate 405 manufactured using PDMS and a lower substrate 410 manufactured using glass. The upper substrate 405 including the upper and side walls of the microchannel 415 can be formed using previously described techniques. Alternatively, or in addition, the upper wall can include multiple grooves 440, each formed in an asymmetric "V" shape. In some implementations, symmetric grooves 440 and asymmetric grooves 445 can be interspersed in the herringbone pattern. Each groove further includes an apex 445 and two ends 450 and 455. In addition, the micro-channel 415 includes two side walls 420 and 425.

To configure the microfluidic device 400 to capture the biological analyte of interest, an adherent 460 is disposed on the inner surfaces of the micro-channel 115. Specifically, surface modification is performed on the inner surfaces. In some implementations, as shown in FIG. 4B, the adherent 460 can be mixed in a solution and flowed through the micro-channel 415. As the solution flows through the micro-channel 415, the adherent 460 binds to, and is thereby disposed in the inner surfaces of the channel 415.

Techniques other than flowing the adherent through the micro-channel 115 can also be used to dispose the adherent. For example, in implementations in which plastic substrates are employed, the adherent can be disposed on the substrate, for example, by ultra-violet (UV) radiation treatment to alter the surface properties such that analytes bind to the altered surface prior to bonding the upper and lower substrates. In implementations in which the lower substrate is glass, the glass can be functionalized, for example, by sputtering, by gas phase deposition, by building up layers of nanoparticle monolayers, and the like prior to bonding the glass substrate to the upper substrate.

As shown in FIG. 4C, the adherent 460 can be disposed throughout the inner surfaces of the micro-channel 415. Alternatively, the adherent 460 can be disposed in one or more walls of the micro-channel 415, for example, in the wall in which the grooves 445 are formed. In some embodiments, the adherent 460 can be disposed only on a lower substrate 410 manufactured from glass. In such embodiments, the lower substrate 410 can be bonded to the upper substrate 405 after the adherent is disposed on the lower substrate. In such implementations, the flow rate of the fluid is selected such that the microvortices established by the grooves 440 drive the cells in the fluid toward the lower substrate 410 increasing a number of cell-lower substrate 410 interactions. Subsequently, the lower substrate 410 can be separated from the upper substrate 405 and the captured cells can be cultured.

In some implementations, the adherent 460 can be selected such that the micro-channel 415 can be used for affinity-based cell capture utilizing wet chemistry techniques. In such implementations, the adherent 460 can be an antibody, for example, antibody for EpCAM, or an aptamer, for example, aptamer for surface proteins, with which the inner surfaces of the micro-channel 415 are functionalized. Additional examples of adherent 460 include avidin coated surfaces to capture amplified target cells that express biotin through the biotin-avidin linkage. Further examples of adherents corresponding to cells that can be captured are shown in Table 1 below.

TABLE 1

| Cell-type | Adherent |
| --- | --- |
| Neutrophil | Anti-CD66 |
| Monocyte | Anti-CD14 |
| Lymphocyte | Anti-CD4; Anti-CD8 |
| Circulating tumor cells | Anti-EpCAM |
| Neutrophils | E, P Selectins |
| HIV-specific T cell | HAL A2-SL9 |
| Any disease specific T cell | Pentamer |

Once functionalized, the inner surfaces function as capture devices that can bind the analytes of interest. Capture efficiencies of exemplary microfluidic devices are described with reference to FIG. 5.

EXAMPLE 1

Capture Efficiency

Figure 5:
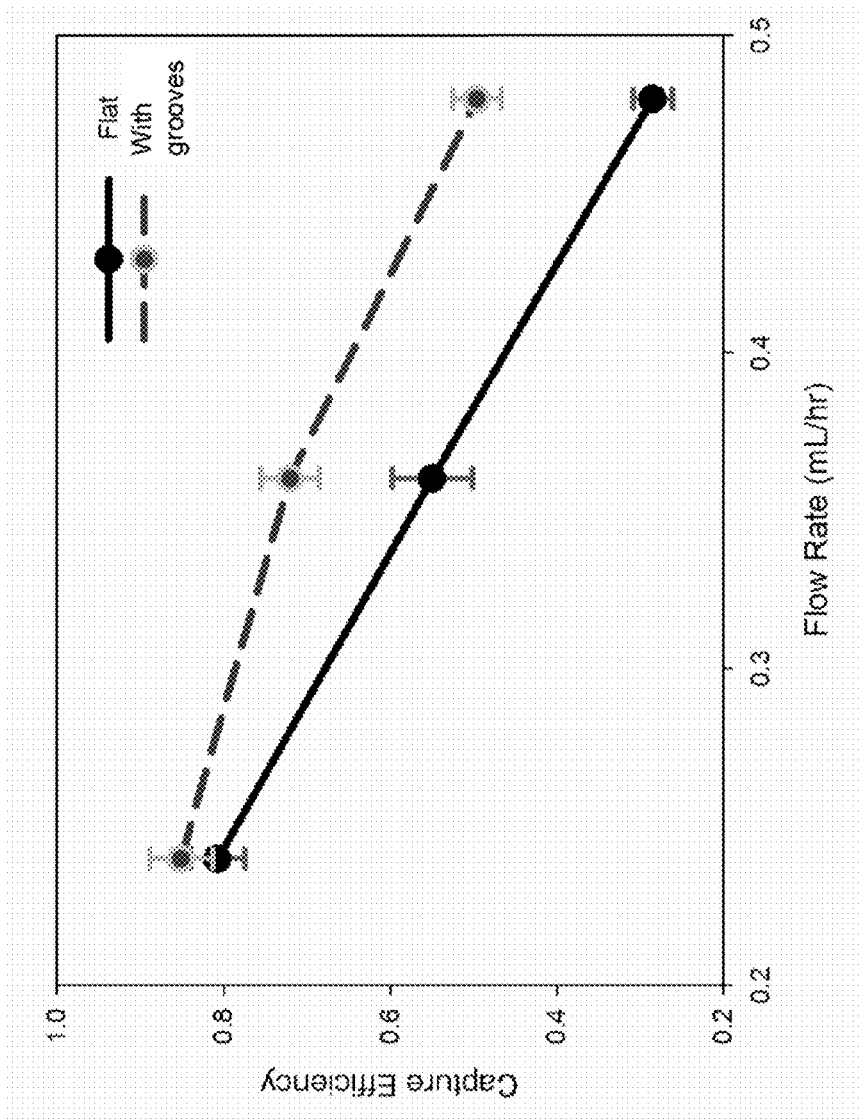
FIG. 5 shows capture efficiencies of example microfluidic devices for different flow rates.

FIG. 5 shows capture efficiencies of example microfluidic devices for different flow rates. As described previously, the inner surfaces on which the adherent 460 are disposed bind cells that interact with the surfaces. To study the capture efficiency of microfluidic devices, a buffer solution spiked with cancer cells (lung cancer cells—H1650 line) was flowed through a microfluidic device 400 having herringbone patterns in the upper wall and microfluidic device 200 having flat wall surfaces. The microfluidic device 400 used in this example is a small footprint design having a width of 2 mm and a length of 2 cm. The fluids were flowed through the micro-channel 415 of the device 400 at flow rates of 0.12 ml/hr, 0.24 ml/hr, 0.36 ml/hr, and 0.48 ml/hr. All fluids that traveled through the microfluidic devices 200 and 400 were collected into a specially designed, serpentine waste chamber. Cell capture efficiency was determined by counting the number of cells captured in the devices (flat 200 or herringbone 400) and dividing that number by the total number of cells put through the device (counting the cells in the waste chamber and adding that to the number of cells captured in the device).

For these experiments, three different flow rates were studied, with four data points taken for each condition. It is desirable that a device provide a high capture efficiency at high flow rates. This can reduce the time and sample size required to capture a desired number of cells of interest. As shown in FIG. 5, the microfluidic device 400, that included the herringbone pattern, outperformed the microfluidic device 200, that has only flat surfaces, in cell capture efficiency for all flow rates. As flow rates increase, the advantage of the device 400 with the herringbone pattern increased. Even at very high flow rates, the capture efficiency for the device 400 with the herringbone patterns was ~50%, whereas for the device 200 without the grooves, it dropped to ~30%.

EXAMPLE 2

Capture Efficiency

Figure 6:
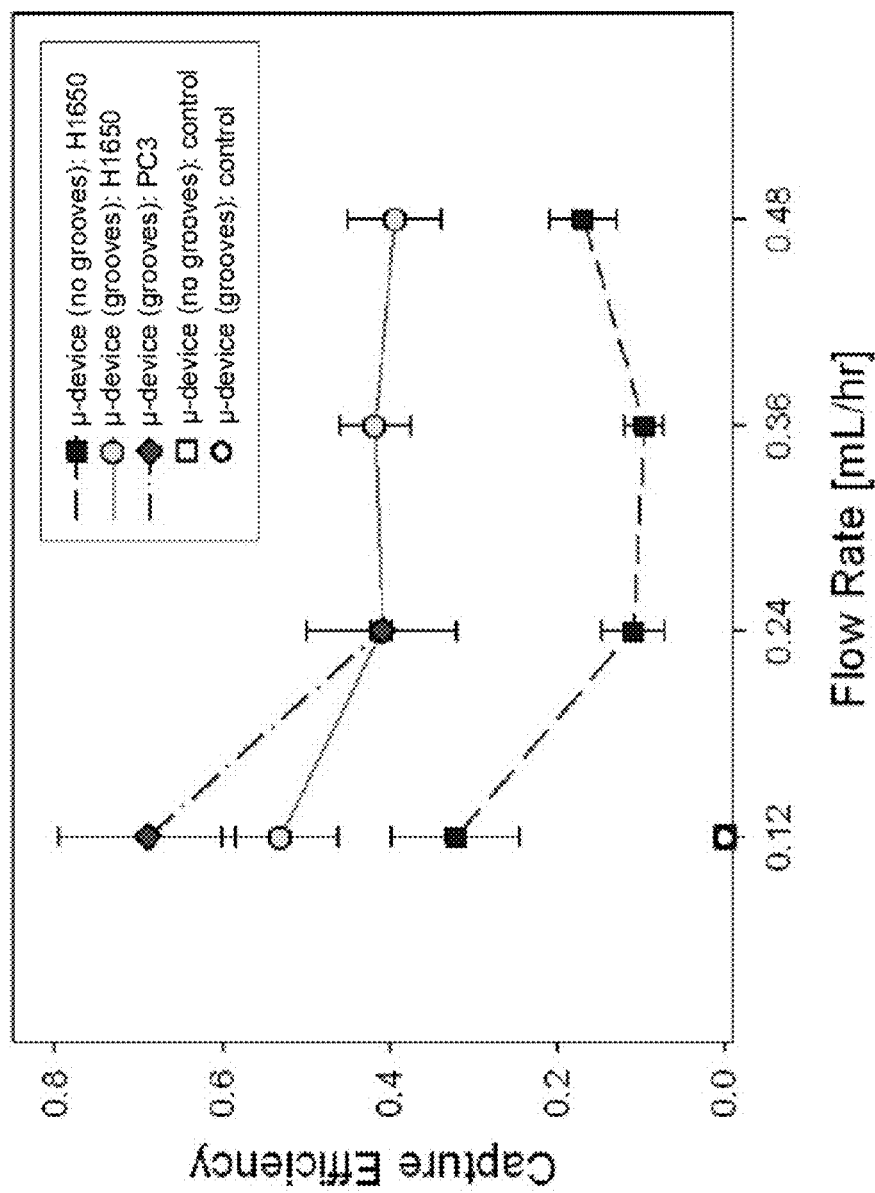
FIG. 6 shows capture efficiencies of cancer cells spiked in whole blood.

FIG. 6 shows capture efficiencies for example microfluidic devices with and without grooves. Similar to the previously described experiments, the microfluidic device 200 having flat surfaces and the device 400 having the herringbone pattern were compared by determining the capture efficiency of cancer cells spiked into whole blood (5,000 cells/ml). The microfluidic device 400 used in this example was the small footprint design described with reference to FIG. 5. Four different flow rates, similar to the flow rates described with reference to Example 1, were explored. In addition, control microfluidic devices, one including the herringbone pattern and the other including the flat surfaces, were tested. In addition, the control microfluidic devices were also tested by functionalizing with an irrelevant capture antibody not configured to capture the cancer cells. For both control microfluidic devices, zero cell capture was observed. Similar to the previous results associated with cancer cells in the buffer solution, the capture efficiency with the microfluidic device 400 having the herringbone pattern was better than the microfluidic device 200 having the flat surfaces, for all conditions tested.

Further, a cell line of prostate cancer cells (PC3) was tested due to the reduced EpCAM express. Cancer cells have less EpCAM than regular epithelial cells. The new cell line and their expression level is approximately 40,000 EpCAM molecules/cell. The number of cells spiked into blood were 1,000 cells/ml so that the spiking numbers are more relevant to rare cell detection levels. For the new cell line, experiments were conducted at flow rates of 0.12 ml/hr and 0.24 ml/hr. For the PC3, the EpCAM surface express was decreased by an order of magnitude relative to the cancer cells and the spiking concentration was reduced by a factor of five. Nevertheless, capture efficiencies comparable to the H1650s are observed using the microfluidic device 400.

EXAMPLE 3

Cell Viability

Figure 7:
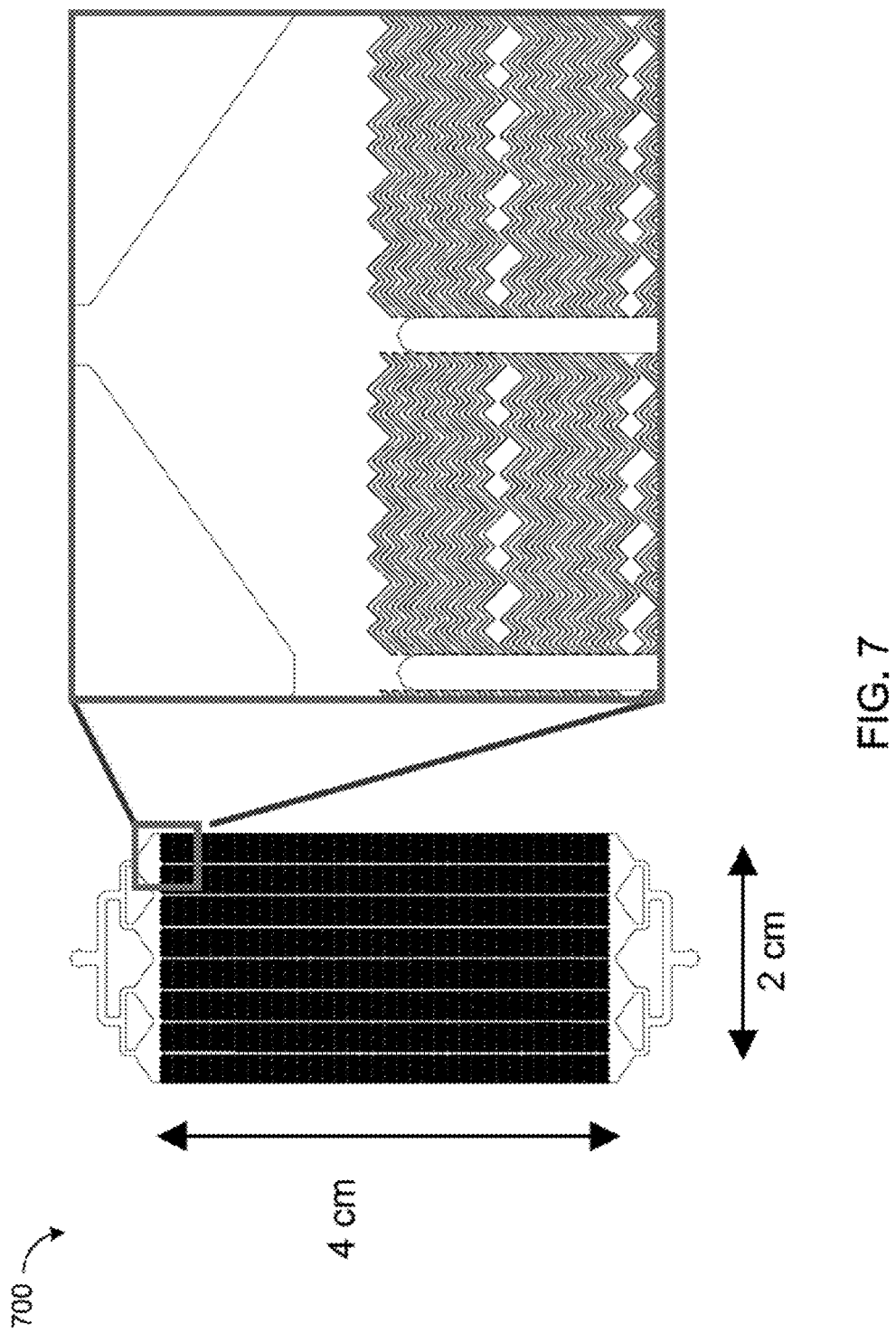
FIG. 7 shows an embodiment of a high throughput microfluidic device having columns of herringbone patterns.

The effect of flow patterns and subsequent higher shear stress on viability of the captured cells was also studied using traditional Live/Dead assays. Cancer cells spiked into whole blood were captured in the micro-channel 415 of a high throughput microfluidic device 700, as shown in FIG. 7, having columns of herringbone patterns. The microfluidic device 400 represents a small footprint version that can be used for initial validation studies. The microfluidic device 700 is an example of a scaled-up version of the microfluidic device 400. To scale up the device, the design of the microfluidic device 400 was repeated and elongated. In some embodiments, the microfluidic device 700 is 2 cm wide and 4 cm long and includes a header region and a footer region. In this example, multiple herringbone patterns were formed by forming columns of herringbone patterns adjacent to each other in an upper wall of a micro-channel having a larger width than the micro-channel 415. The volumetric flow rate through the micro-channel 715 is 2 ml/hr. captured cells were stained on the substrate to which the cells were bound with Calcein AM and Ethidium Homodimer. Results indicated that the most (~90%) of the captured cells were viable, demonstrating that the herringbone pattern had limited negative effects on the captured cells under these conditions.

In some embodiments, the cells can be separated from the substrate and cultured separately. To separate the cells from the adherents, the linkage can between the adherents and the cells can be weakened, for example, by dissolving the adherents in a solution that does not affect the cells.

The number of columns of herringbone patterns was limited only by the width of the micro-channel. In some implementations, the microfluidic device 700 includes eight mini-chambers, i.e., eight columns of herringbone patterns. In such implementations, a header design can be incorporated at an inlet of the micro-channel to provide stability and uniform fluid volumes to each column of herringbone patterns. In some implementations, each column of herringbone patterns is positioned next to an adjacent column of patterns such that, an apex of a "V" shaped groove in the column is aligned with an apex of the "V" shaped groove in the adjacent column. In other words, the apexes of both grooves lie on a line perpendicular to a principal axis passing through the micro-channel of the microfluidic device 700. If all grooves in a column are equidistantly formed in the micro-channel of the device 700, then all grooves in the device 700 will be aligned with each other. In some implementations, a column of herringbone patterns can be offset from an adjacent column. For example, the apex of a "V"-shaped groove in the column can be offset by 10 μm from the apex of a "V"-shaped groove in the adjacent column. The offset column design can further promote mixing. In some implementations, the multiple columns in the device 700 can include symmetric grooves 335 and asymmetric grooves 340 randomly interspersed in each column. The forming of interspersed grooves promotes transverse movement of the fluid and the particles suspended in them, thereby increasing the number of cell-micro-channel wall interactions and consequently increasing cell capture.

EXAMPLE 4

Cell Culturing

Figure 8:
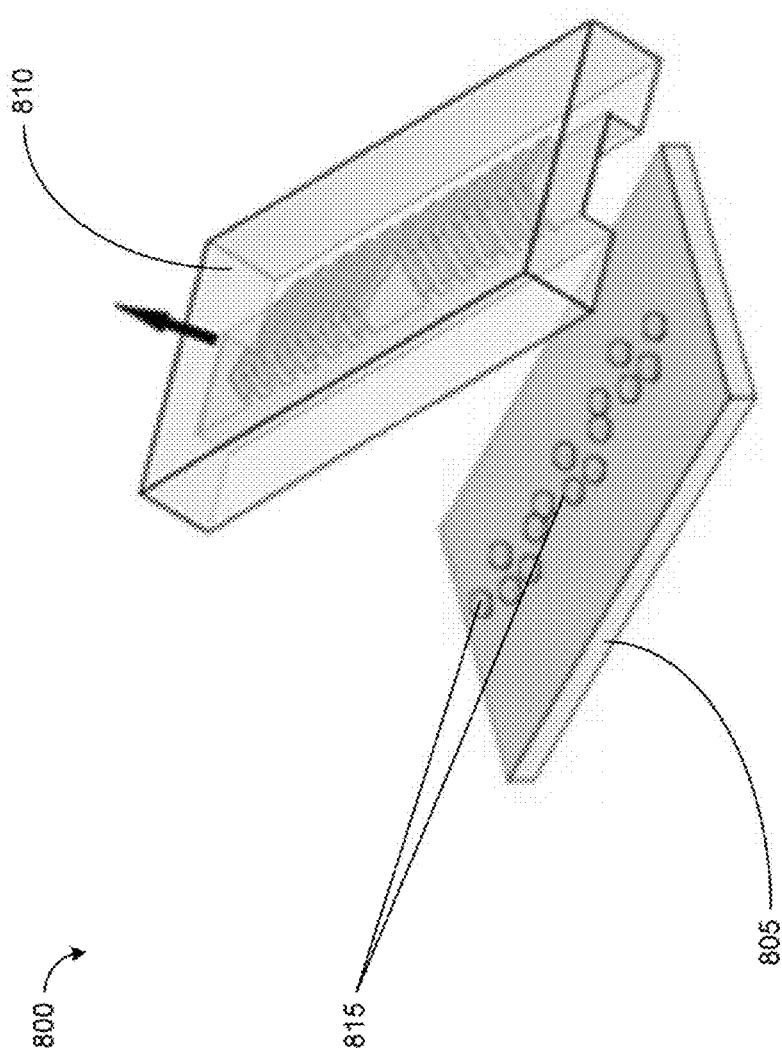
FIG. 8 shows an embodiment of a microfluidic device for culturing captured cells.

In another example, a microfluidic device 800 for culturing captured cells as shown in FIG. 8 was used to capture and culture cells. The microfluidic device 800, was similar to the high throughput design described with reference to FIG. 7, and included a lower substrate manufactured using glass and an upper substrate 810 manufactured using PDMS that included the columns of herringbone patterns as described previously. The flow rates of blood containing the cells to be captured were around 2 ml/hr and were manipulated to cause the cells to contact adhere to the lower glass substrate 810. In the microfluidic device 800, the both the lower and the upper substrates were coated with adherent. The lower and upper substrates were reversibly bonded to each other using such that, subsequent to cell capture, the upper substrate 810 could be removed from the lower substrate 805, for example, by applying mechanical forces. In other embodiments, the lower and upper substrates can be mechanically clamped to form a water-tight seal or by suitable methods that do not damage the bound cells. In some embodiments, the adherent 460 can be disposed on either the lower or the upper substrate. Cells can be captured on the substrate on which the adherent is disposed.

Figure 9A:
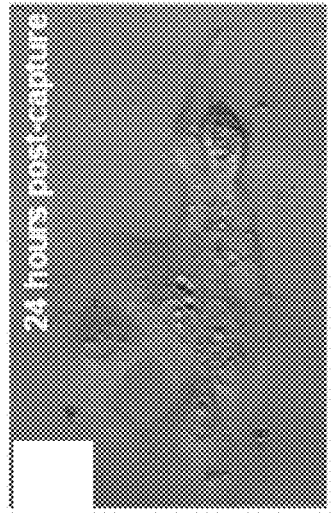
FIGS. 9A-9C are micrographs showing the growth of captured cells on a glass substrate.
Figure 9B:
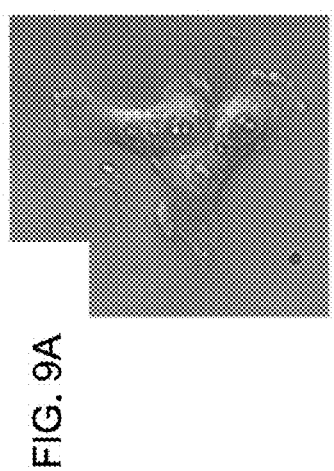
Figure 9C:
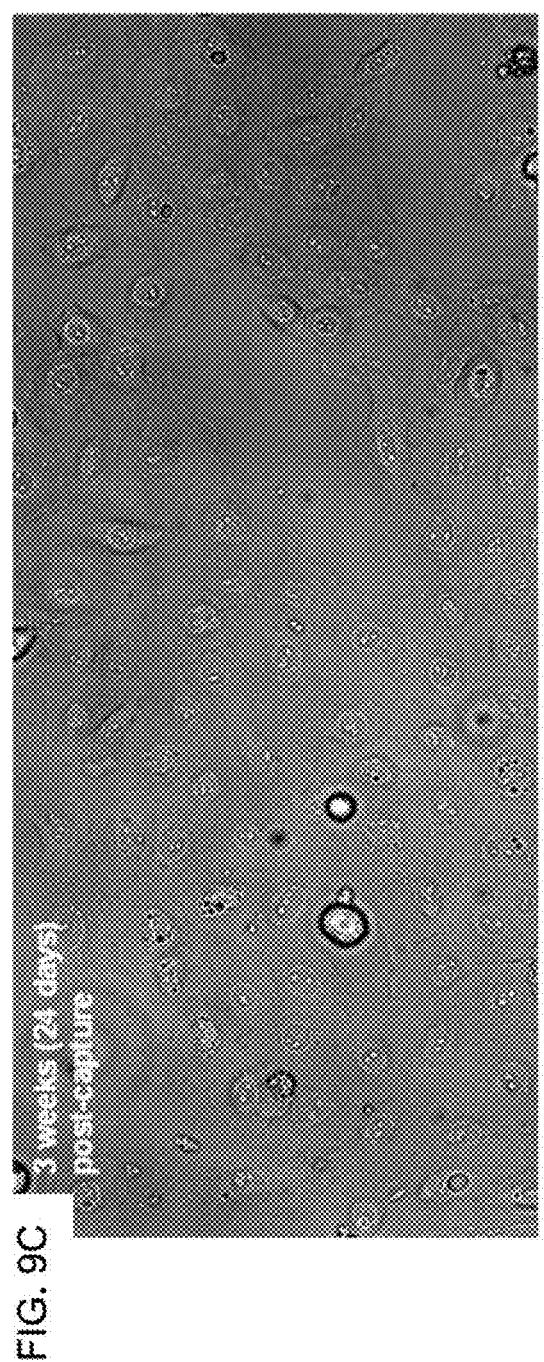

FIGS. 9A-9C are micrographs showing the growth of captured cells on a glass substrate. Following capture of the cancer cells spiked into blood, the upper substrate 810 of the microfluidic device 800 was removed and both upper and lower substrates were placed into a petri dish and incubated at 37° C., 5% $CO_2$ with the appropriate cell culture media (FIG. 9A). As shown in FIG. 9B, the cells were adhering to the substrate and had started to spread and increase in number within 24 hours. After more than three weeks of cell culture, the cells continued to divide, forming a monolayer on both the lower substrate (glass) and the upper substrate (PDMS). At this point, the cells were removed from the capture surfaces (via trypsinization) and cultured in traditional cell culture flasks. In this manner, successful culture of captured cancer cells for extended periods of time was demonstrated. Thus, the cells were not only viable but also functional and can be grown in culture.

EXAMPLE 5

Phenotype Changes

Figure 10:
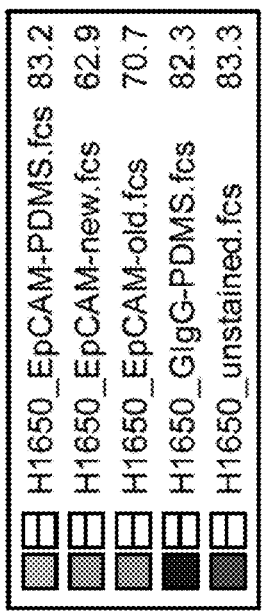
FIG. 10 shows an analysis of EpCAM expression on the cells captured with the microfluidic device having grooves and control cells.
Figure 10:
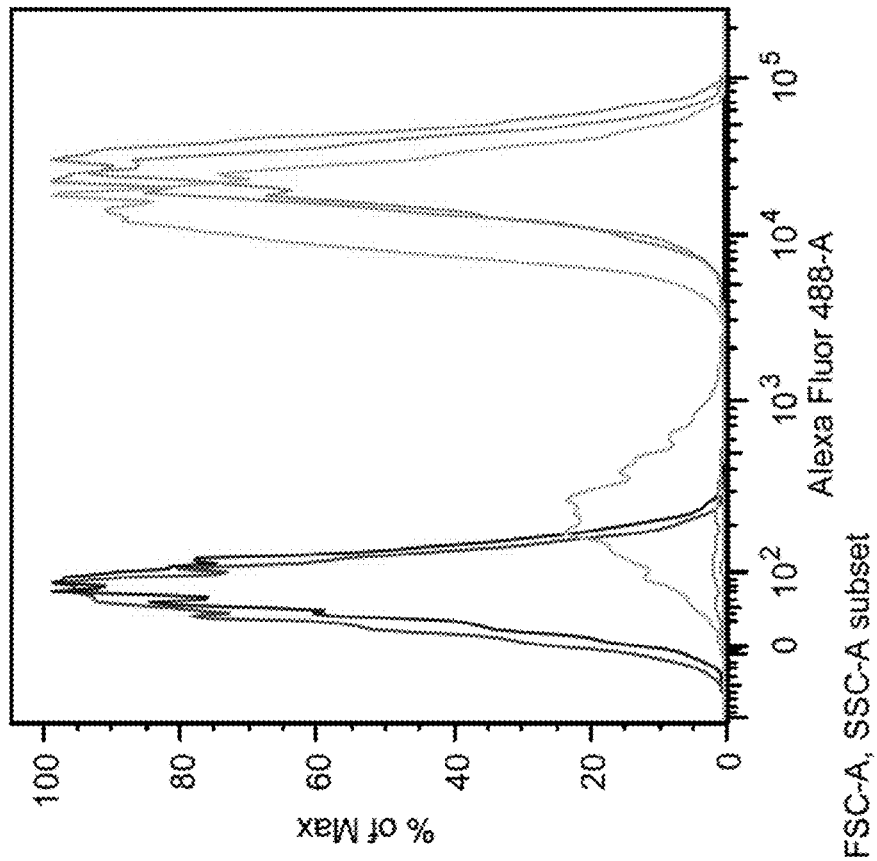

FIG. 10 shows fluorescence-activated cell sorting ("FACS") analysis of EpCAM expression on the cells captured with the microfluidic device having grooves and control cells. To explore if the exposure of the cancer cells to the microfluidic device 800 had any impact on the cell phenotype, one marker, EpCAM, was studied. Specifically, expression levels between the cells captured on the device 800 and the control cells (prepared in the same manner, but never flowed through the device) were compared. Both cell populations were cultured for 3 weeks post-experiment. Flow cytometry results indicated that the capture and culture of the cancer cells did not change their expression levels of EpCAM. These results indicate that capturing with the microfluidic device 800 does not change the phenotype of the cell.

EXAMPLE 6

Cell Capture

Figure 11B:
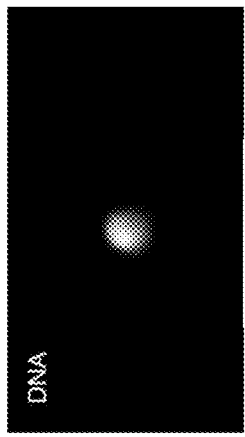
FIGS. 11A-11E show a circulating tumor cell captured from a prostate cancer patient using the microfluidic device.
Figure 11C:
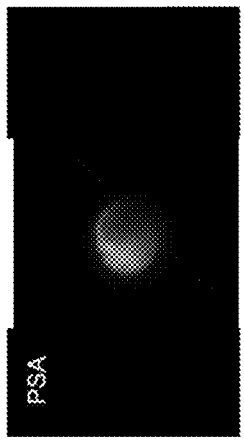
Figure 11D:
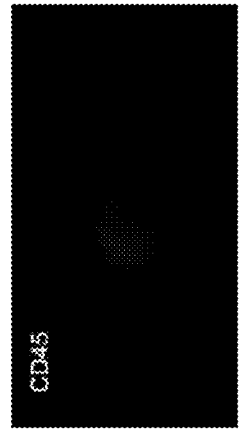
Figure 11A:
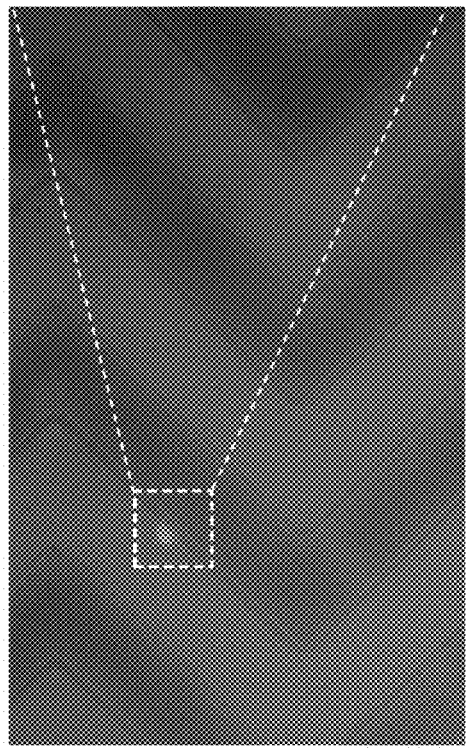
Figure 11E:
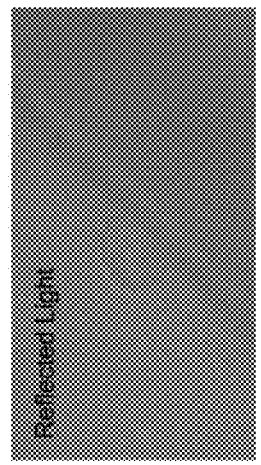

FIG. 11A shows a circulating tumor cell (CTC) captured from a prostate cancer patient using the microfluidic device 100. As shown in FIG. 11A, a CTC was captured on the grooves of the microfluidic device 100. FIG. 11B shows that the cell was intact, demonstrating the intact nucleus and cytoplasm. The cell was identified as a CTC because it stained positive for PSA (prostate-specific antigen, green), and a nuclear stain (DAPI, blue) and negative for CD45 (red), a traditional marker for white blood cells (see FIGS. 11C and 11D for a gray-scale representation). Also, there are no contaminating cells. FIG. 11E shows the intact cell under reflected light.

EXAMPLE 7

Background CTC Levels

Figure 12:
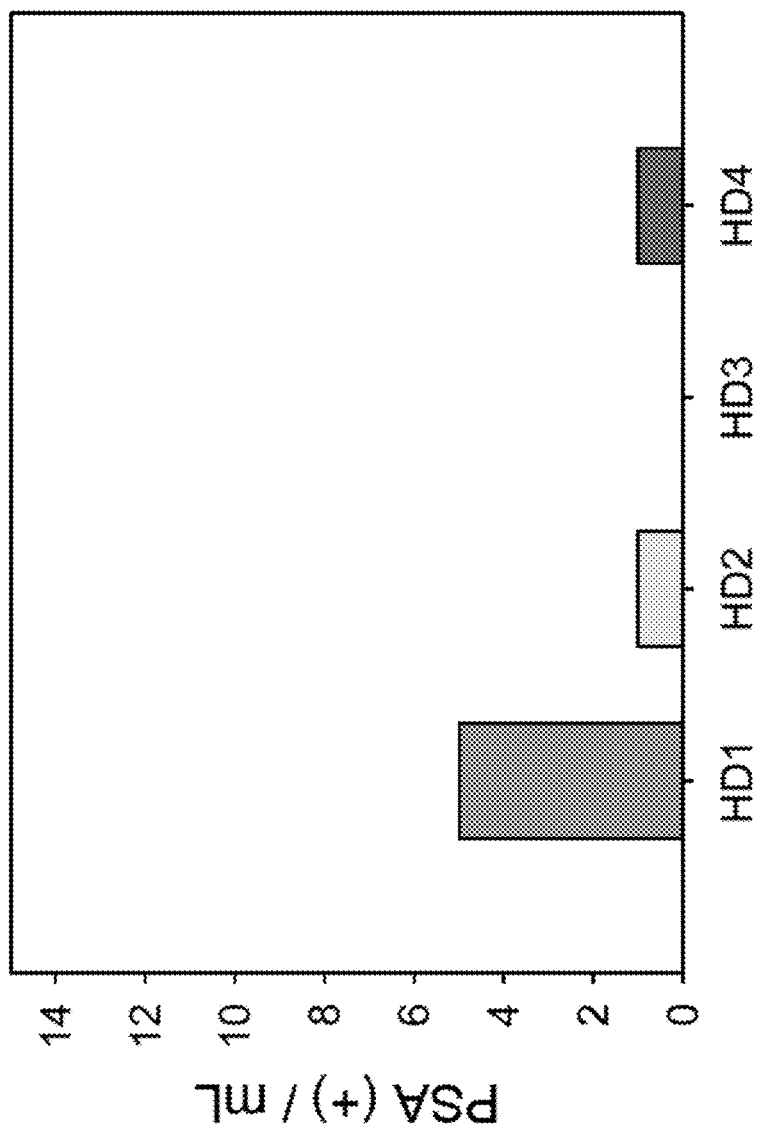
FIG. 12 show healthy donor controls.

FIG. 12 show healthy donor controls. To confirm that the CTC counts observed using patient samples were higher than the background that would be observed in healthy donor samples, four distinct donors (3 male, 1 female) were tested using the microfluidic device 100 and stained with the PSA/CD45 stain. For all four cases, the healthy donor counts were ≤5 false positives/mL, with an average of 2 false positives/mL. Similar experiments with the silicon chip resulted in a higher number of false positives, presumably due to the increase in non-specific binding.

EXAMPLE 8

Capture Levels

Figure 13:
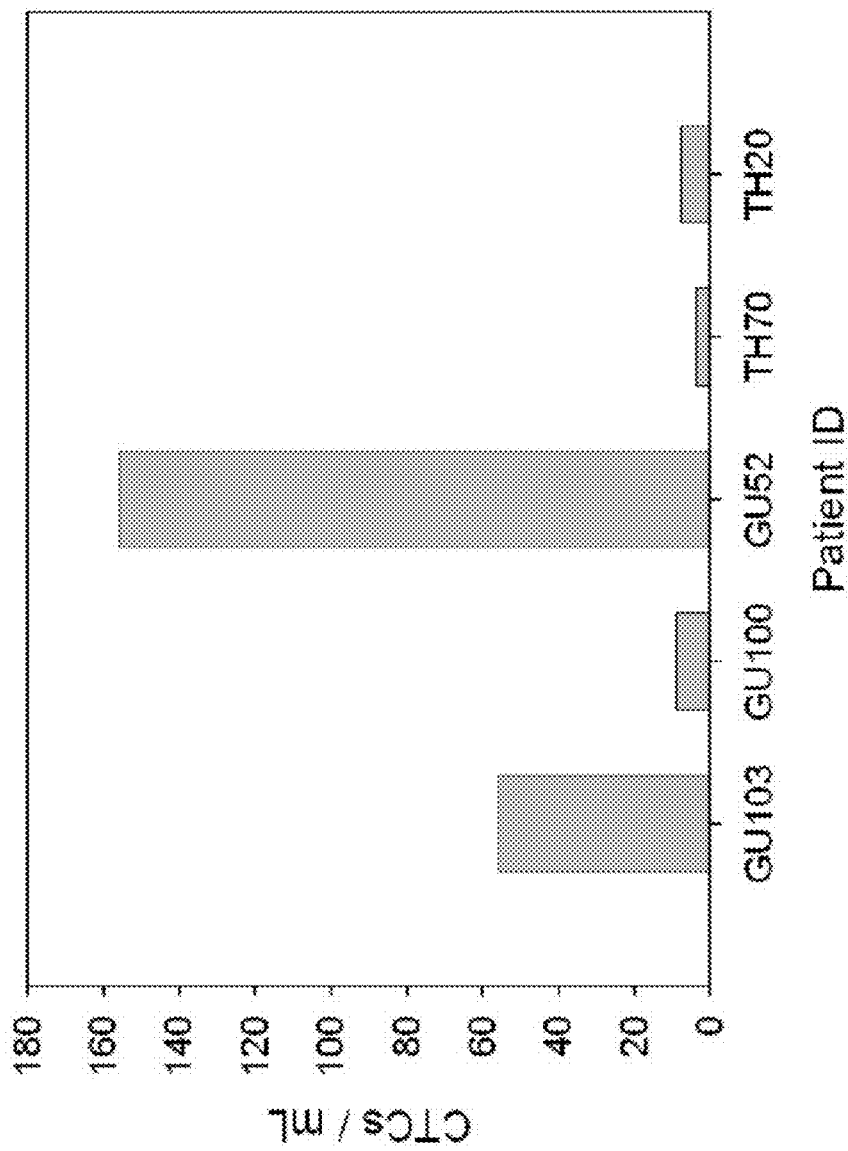
FIG. 13 shows CTC capture from patient samples using the microfluidic device having grooves.
Figure 14A:
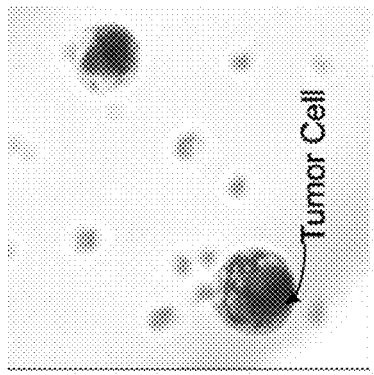
FIGS. 14A-14D shows Wright-Giemsa staining of CTCs in the microfluidic device having grooves.
Figure 14B:
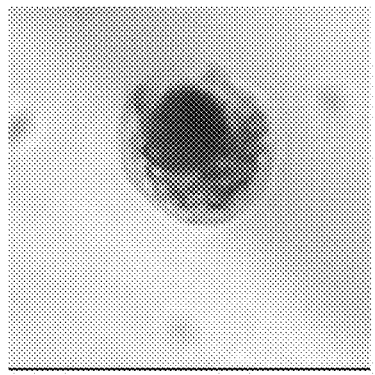
Figure 14C:
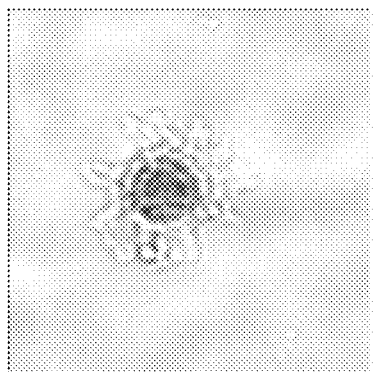
Figure 14D:
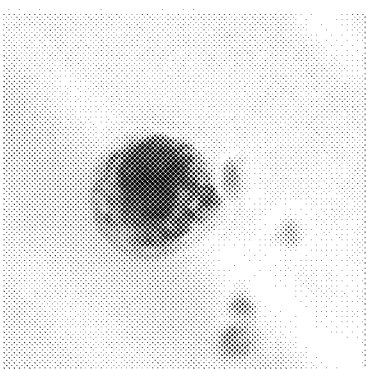

FIG. 13 shows CTC capture from patient samples using the microfluidic device 100 having grooves. Initial results indicate that CTC capture from patient samples when using the microfluidic device 100 having grooves can be as high as 160 CTCs/mL.

FIGS. 14A-14D show gray-scale representations of Wright-Giemsa staining of CTCs in the microfluidic device 100 having grooves. Because the substrates used to manufacture the microfluidic device 100 are transparent, the patient samples captured within the microfluidic channel 115 can be stained with histological stains, for example, Wright-Giemsa. FIGS. 14A-14D show micrographs taken from a lung cancer patient sample run through the microfluidic device 100. The cells selected are CTCs.

Figure 15:
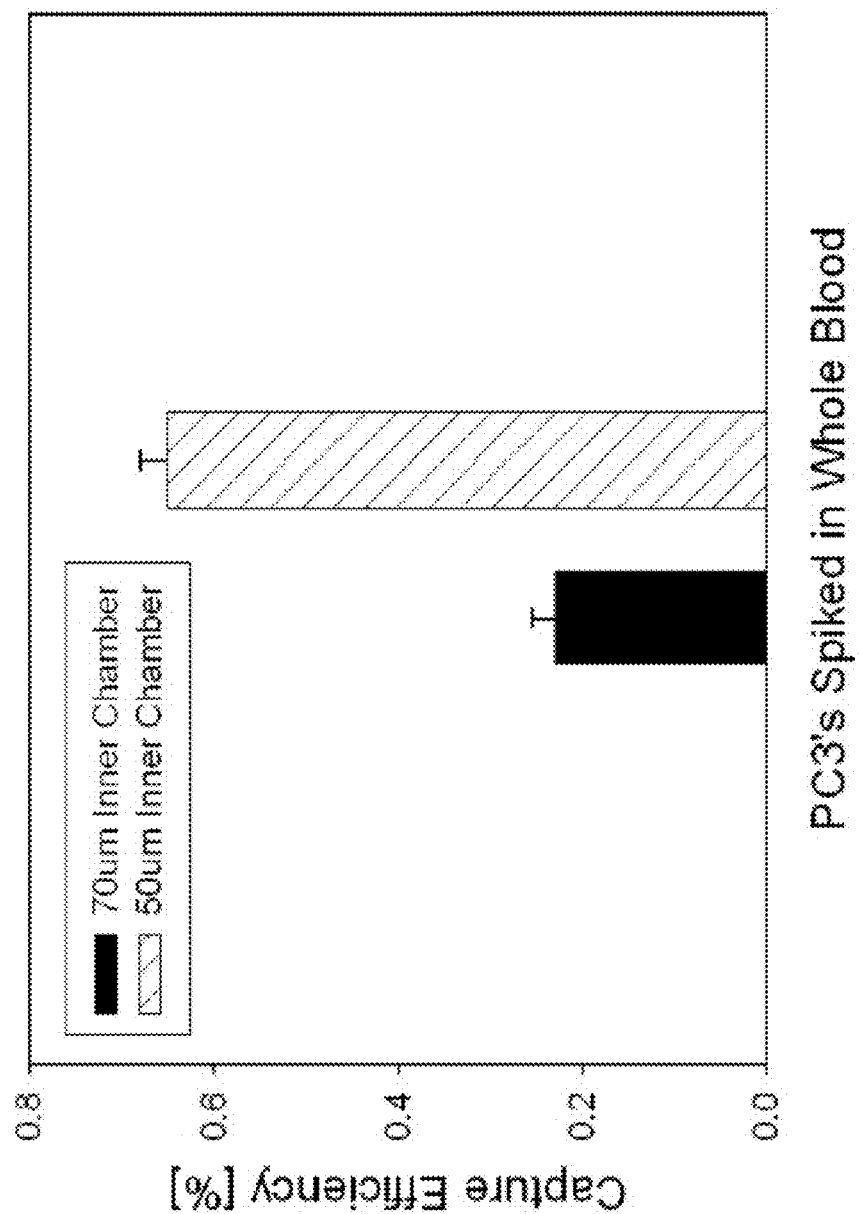
FIG. 15 shows a comparison of two microfluidic devices having different groove dimensions.

FIG. 15 shows a comparison of two microfluidic devices having different groove dimensions. Two microfluidic devices were compared to determine an effect of a height of the groove on capture efficiency. A first microfluidic device had a channel height of 70 µm and a second microfluidic device had a channel height of 50 µm. The first microfluidic device had a groove height of 35 µm and the second microfluidic device had a channel height of 25 µm. In comparison to the first microfluidic device, the second microfluidic device exhibited a three fold increase in capture efficiency with the low expressor cells, PC3, spiked into whole blood.

While this specification contains many specifics, these should not be construed as limitations on the scope of the specification or of what may be claimed, but rather as descriptions of features specific to particular implementations of the specification. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Thus, particular implementations of the specification have been described. Other implementations are within the scope of the following claims. For example, the actions recited in the claims can be performed in a different order and still achieve desirable results.

Cells disposed in blood or in buffer solution can be flowed through the micro-channel in such an orientation to bind to adherents disposed in the channel. Techniques such as hot embossing, injection molding, and the like can be used form the micro-channel or the grooves or both. In such embodiments, the master, from which the substrates are manufactured, need not be silicon. In some embodiments, small molecules such as peptides, nucleotides, and the like can be used as adherents In some embodiments, prior to flowing any blood through a micro-channel, non-specific binding can be reduced by the addition of a surfactant to a blocking buffer (typically 1-3% BSA in 1×PBS). After adding the blocking buffer (e.g., 0.05% TWEEN20 in 3% BSA in 1×PBS), the microfluidic device can be incubated for a duration, for example, one hour, at a temperature, for example, room temperature, to provide efficient blocking of the substrates. Blood flow can be initiated following the blocking step.

In some embodiments, decreasing the non-specific binding to a surface of the micro-channel can be achieved by contacting the surface comprising the analyte-binding moiety with a nonionic detergent prior to sample contact with the surface. The nonionic detergent can be a polysorbate surfactant such as a polyoxyethylene derivative of sorbitan monolaurate (for example, polysorbate 20, sold under the tradename TWEEN20). The nonionic detergent can be contacted with the surface at a concentration lower than the concentration required to lyse mammalian cells. For example, an aqueous solution comprising polysorbate 20 at a concentration of up to about 0.05% can be used to pre-treat a surface before contact with a biological sample.

The aqueous solution can further comprise components to reduce non-specific surface binding from blood components. For example, the surface can be contacted with a mixture of 0.05% polysorbate 20, 1% BSA and 1× phosphate buffered saline (PBS) (calcium ion and magnesium ion—free). The volume of the pre-treatment solution can be selected based on the dimensions of the channel. For example, about 3 mL of the 0.05% polysorbate 20 solution described above can be passed through a microfluidic channel at a rate of about 30 ml/hr. The microchannel can be incubated in the polysorbate 20 solution for about 1 hour before introducing the biological sample to the channel.

In some embodiments, the micro-channel having a surface containing a biotin-binding conjugate is contacted with a solution comprising 0.05% Tween20 in 1% BSA in 1×PBS (Ca2+/Mg2+—free) (for example, 3 mL of the surfactant solution at a flow rate of about 30 mL/hr) prior to contact with the biological sample containing CTCs, a biotinylated EpCAM antibody, biotin and streptavidin. Pluronics, poloxymer, PEG, and other similar surfactants can be similarly used instead of or in combination with polysorbate 20.

What is claimed is:

1. A method for capturing particles suspended in a fluid flowed through a micro-channel, the method comprising:
    flowing the fluid including the particles to be captured through a micro-channel in a first direction and past a first groove defined in a surface of a first wall of the micro-channel,
        wherein the first groove comprises an apex and two arms connected to the apex in a V-shape arranged in a plane parallel to the first wall, and wherein the first V-shaped groove is oriented such that the apex points in the first direction of flow through the micro-channel or opposite to the first direction of flow through the micro-channel, and
        wherein an adherent that binds selectively to particles of interest is disposed on a surface of the first groove;
    contacting at least some of the particles against the adherent disposed on the surface of the first groove; and
    capturing at least some of the particles contacting the adherent.

2. The method of claim 1, comprising flowing the fluid including the particles to be captured past a second groove defined in a surface of a second wall of the micro-channel.

3. The method of claim 1, wherein the two arms of the first groove are symmetric.

4. The method of claim 1, wherein the two arms of the first groove are asymmetric.

5. The method of claim 1, wherein an angle between each arm of the first groove is between 10° and 170°.

6. The method of claim 1, wherein the micro-channel comprises a second groove defined in the surface of the first wall, wherein the second groove comprises an apex and two arms connected to the apex in a V-shape arranged in a plane parallel to the surface of the first wall, and
    wherein the apex of the first groove is laterally offset to a first side of a centerline of the microfluidic channel, and the apex of the second groove is laterally offset to a second opposite side of the centerline.

7. The method of claim 1, wherein the adherent is an antibody.

8. The method of claim 7, wherein the antibody is an anti-CD66 antibody, an anti-CD14 antibody, an anti-CD4 antibody, an anti-CD8 antibody, or an anti-EpCAM antibody.

9. The method of claim 1, wherein the adherent is an aptamer.

10. The method of claim 1, wherein the fluid sample is blood.

11. The method of claim 1, wherein the particles to be captured comprise cells.

12. The method of claim 11, wherein the cells comprise cancer cells.

13. The method of claim 1, wherein the adherent comprises an antibody, an aptamer, a pentamer, a selectin, an avidin, a biotin, a nucleotide, or a peptide.

14. The method of claim 1, wherein flowing the fluid past the first groove forms microvortices in the fluid.

* * * * *

UNITED STATES PATENT AND TRADEMARK OFFICE
CERTIFICATE OF CORRECTION

PATENT NO. : 10,126,218 B2
APPLICATION NO. : 14/843028
DATED : November 13, 2018
INVENTOR(S) : Mehmet Toner, Shannon Stott and Chia-Hsien Hsu It is certified that error appears in the above-identified patent and that said Letters Patent is hereby corrected as shown below:

In the Specification

Column 1, Line 15, insert -- STATEMENT OF FEDERALLY SPONSORED RESEARCH
This invention was made with government support under Grant Nos. EB002503, and EB008047 awarded by the National Institutes of Health. The government has certain rights in the invention. --

Signed and Sealed this
Twenty-third Day of May, 2023

Katherine Kelly Vidal
*Director of the United States Patent and Trademark Office*